United States Patent [19]
Da Prada et al.

[11] Patent Number: 5,238,962
[45] Date of Patent: Aug. 24, 1993

[54] BENZAMIDE DERIVATIVES

[75] Inventors: Mosé Da Prada; Renato Joos, both of Riehen; Emilio Kyburz, Reinach; Pierre C. Wyss, Muttenz, all of Switzerland

[73] Assignee: Hoffmann-La Roche Inc., Nutley, N.J.

[21] Appl. No.: 896,747

[22] Filed: Jun. 9, 1992

Related U.S. Application Data

[63] Continuation of Ser. No. 668,002, Mar. 12, 1991, abandoned, which is a continuation of Ser. No. 505,874, Apr. 5, 1990, abandoned, which is a continuation of Ser. No. 206,986, Jun. 10, 1988, abandoned, which is a continuation of Ser. No. 585,732, Mar. 2, 1984, abandoned.

[30] Foreign Application Priority Data

Mar. 3, 1983 [CH] Switzerland ............ 1150/83

[51] Int. Cl.$^5$ .......................... A61K 31/165
[52] U.S. Cl. ..................... 514/617; 564/183
[58] Field of Search ............ 564/183; 514/617

[56] References Cited

U.S. PATENT DOCUMENTS

| | | | |
|---|---|---|---|
| 2,785,200 | 3/1957 | Moore | 564/183 |
| 3,342,679 | 9/1967 | Paulshock | 564/183 |
| 3,591,634 | 7/1971 | Thominet | 564/183 |
| 3,644,644 | 2/1972 | Thominet | 564/183 |
| 3,823,134 | 7/1974 | Houlihan | 564/183 |
| 3,825,594 | 7/1974 | Houlihan | 564/183 |
| 3,928,412 | 12/1975 | Smith | 564/183 |
| 3,933,911 | 1/1976 | Main | 564/183 |
| 3,959,369 | 5/1976 | Smith | 424/321 |
| 4,034,106 | 7/1977 | Smith | 564/183 |
| 4,117,157 | 9/1978 | Smith | 564/183 |
| 4,131,685 | 12/1978 | Smith | 564/183 |
| 4,186,135 | 1/1980 | Thominet | 59/436 |
| 4,425,362 | 1/1984 | Berthold et al. | 514/522 X |

FOREIGN PATENT DOCUMENTS

| | | |
|---|---|---|
| 83729 | 7/1983 | European Pat. Off. |
| 2542702 | 4/1977 | Fed. Rep. of Germany |
| 2616486 | 11/1977 | Fed. Rep. of Germany |

OTHER PUBLICATIONS

J. Phar. Pharmacol ('81) 33, 145–9, Panmatier et al.
J Med Chem (1964) 7(4), 500–3, Kraml et al.
Arzmeinittel-forsch (1960) 10, 743–5, Demolis et al.
Helv. Chem Acta (1983) 66(2n), 542–6, Anker et al.
JACS 61(1939), 822–5, Hill et al.
Wagner & Zook, Synthetic Organic Chemistry (1953) pp. 567–,665–666, 671.
Bischoff et al., Eur. J. Pharm., 79(1982) 225–232.

Primary Examiner—Glennon H. Hollrah
Assistant Examiner—Brian M. Burn
Attorney, Agent, or Firm—George M. Gould; George W. Johnston; William Krovatin

[57] ABSTRACT

Benzamides of the formula

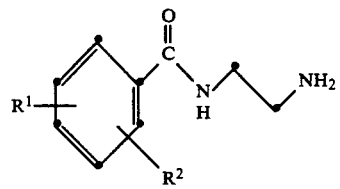

wherein $R^1$ and $R^2$ each independently is hydrogen, halogen, lower alkyl, lower alkoxy, cyano, trifluoromethyl, sulfamoyl, mono(lower alkyl)sulfamoyl or di(lower alkyl)sulfamoyl or $R^1$ and $R^2$ on adjacent carbon atoms together are a methylenedioxy group, with the proviso that $R^2$ is different from hydrogen when $R^1$ are bromine in the 3-position, and their pharmaceutically acceptable acid addition salts have monoamine oxidase inhibiting properties with low toxicity and can accordingly be used for the treatment of depressive states and Parkinsonism.

6 Claims, No Drawings

BENZAMIDE DERIVATIVES

This is a continuation of U.S. application Ser. No. 07/668,002 filed Mar. 12, 1991, which is a continuation of U.S. Ser. No. 07/505,874 filed Apr. 5, 1990, which is a continuation of U.S. Ser. No. 07/206,986 filed Jun. 10, 1988, which is a continuation of U.S. Ser. No. 07/585,732 filed Mar. 2, 1984 all now abandoned.

BRIEF SUMMARY OF THE INVENTION

The invention relates to benzamide derivatives. In particular, it is concerned with N-aminoethyl-substituted benzamides of the formula

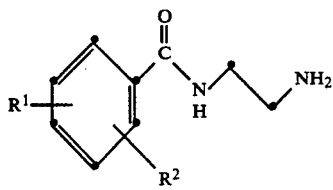

wherein $R^1$ and $R^2$ each independently is hydrogen, halogen, lower alkyl, lower alkoxy, cyano, trifluoromethyl, sulfamoyl, mono(lower alkyl)sulfamoyl or di(lower alkyl)sulfamoyl or $R^1$ and $R^2$ on adjacent carbon atoms together are a methylenedioxy group, with the proviso that $R^2$ is different from hydrogen when $R^1$ is bromine in the 3-position,
and pharmaceutically acceptable acid addition salts thereof. It has been found that the benzamide derivatives of the above formula I and their pharmaceutically acceptable acid addition salts have monoamine oxidase inhibiting properties, and therefore, can be used in the control or prevention of depressive states and Parkinsonism.

DETAILED DESCRIPTION OF THE INVENTION

The invention relates to benzamide derivatives. In particular, it is concerned with N-aminoethyl substituted benzamides of the formula

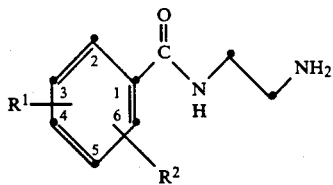

wherein $R^1$ and $R^2$ each independently is hydrogen, halogen, lower alkyl, lower alkoxy, cyano, trifluoromethyl, sulfamoyl, mono(lower alkyl)sulfamoyl or di(lower alkyl)sulfamoyl or $R^1$ and $R^2$ on adjacent carbon atoms together are a methylenedioxy group, with the proviso that $R^2$ is different from hydrogen when $R^1$ is bromine in the 3-position,
and pharmaceutically acceptable acid addition salts thereof.

Some of these compounds are known from, for example, German Offenlegungsschrift 2.458.908, but it has surprisingly been found that they exhibit interesting and therapeutically usable pharmacodynamic properties with low toxicity. Thus, in animal experiments it has been found that the compounds of formula I above and their pharmaceutically acceptable acid addition salts have monoamine oxidase (MAO) inhibiting properties.

Objects of the invention are compounds of formula I and their pharmaceutically acceptable acid addition salts as pharmaceutically active substances, medicaments containing a compound of formula I or a pharmaceutically acceptable acid addition salt thereof, the preparation of such medicaments and the use of compounds of formula I and their pharmaceutically acceptable acid addition salts in the control or prevention of illnesses or in the improvement of health, especially in the control or prevention of depressive states and Parkinsonism.

Of the compounds of formula I above the benzamides of the formula

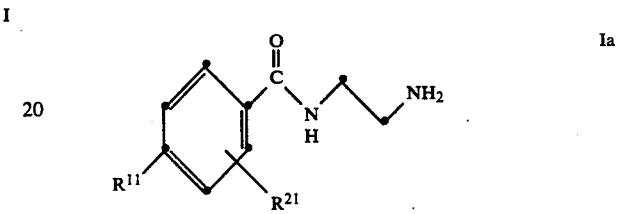

wherein $R^{11}$ is halogen, cyano or trifluoromethyl and $R^{21}$ is hydrogen or $R^{11}$ and $R^{21}$ each is hydrogen or $R^{11}$ and $R^{21}$ on adjacent carbon atoms together are a methylenedioxy group,
and their acid addition salts form part of the present invention.

Another object of the present invention is a process for the preparation of the compounds of formula Ia above their pharmaceutically acceptable acid addition salts.

The term "lower alkyl" used in this description refers to straight-chain and branched-chain hydrocarbon groups containing 1-6, preferably 1-4, carbon atoms such as methyl, ethyl, n-propyl, isopropyl, n-butyl, isobutyl, tert.-butyl and the like. The term "lower alkoxy" refers to lower alkyl ether groups in which the term "lower alkyl" has the above significance. The term "halogen" embraces the four halogens fluorine, chlorine, bromine and iodine. The term "leaving group" signifies in the scope of the present invention known groups such as halogen, preferably chlorine or bromine, arylsulfonyloxy such as, for example, tosyloxy, alkylsulfonyloxy such as, for example, mesyloxy, and the like.

The term "pharmaceutically acceptable acid addition salts" embraces salts with inorganic and organic acids such as hydrochloric acid, hydrobromic acid, nitric acid, sulfuric acid, phosphoric acid, citric acid, formic acid, maleic acid, acetic acid, succinic acid, tartaric acid, methanesulfonic acid, p-toluenesulfonic acid and the like. Such salts can be prepared readily by a person of ordinary skill in the art having regard to the state of the art and bearing in mind the nature of the compound to be converted into a salt.

Preferred compounds of formula I are those in which $R^1$ and $R^2$ each independently is hydrogen, halogen, lower alkyl, lower alkoxy, cyano or trifluoromethyl.

Especially preferred compounds of formula I are those in which $R^1$ and $R^2$ each independently is hydrogen, halogen or lower alkyl.

If the compounds of formula I are disubstituted, then the substituents are preferably situated in the 2,3-, 2,4-, 2,5-, 3,4- or 3,6-position, especially in the 2,4- or 3,4-position, Particularly preferred compounds of formula I are:
N-(2-Aminoethyl)-p-chlorobenzamide,
N-(2-aminoethyl)-p-fluorobenzamide,
N-(2-aminoethyl)-p-bromobenzamide,
N-(2-aminoethyl)-3,4-dichlorobenzamide,
N-(2-aminoethyl)-2,4-dichlorobenzamide and
N-(2-aminoethyl)benzamide, The compounds of formula Ia and their pharmaceutically acceptable acid addition salts can be manufactured in accordance with the invention by
a) reacting a compound of the formula

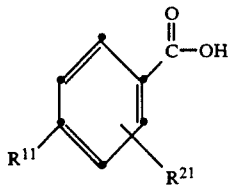

II wherein $R^{11}$ and $R^{21}$ are as described above
in the form of the free acid or in the form of a reactive functional derivative thereof with ethylenediamine, or
b) reacting a compound of the formula

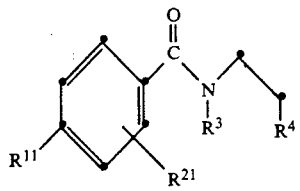

III wherein $R^{11}$ and $R^{21}$ are as described above, $R^3$ is hydrogen and $R^4$ is a leaving group or $R^3$ and $R^4$ together are an additional bond,
with ammonia, or
c) converting the group $R^5$ in a compound of the formula

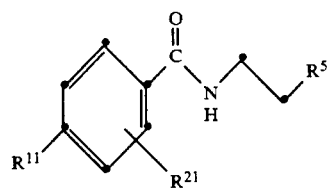

IV wherein $R^{11}$ and $R^{21}$ are as described above and $R^5$ is a group convertible into the amino group,
into the amino group, and, if desired, converting a compound obtained into a pharmaceutically acceptable acid addition salt.

As reactive functional derivatives of the acids of formula II there come into consideration, for example, halides (e.g. chlorides), symmetric or mixed anhydrides, esters (e.g. methyl esters, p-nitrophenyl esters or N-hydroxysuccinimde esters), azides and amides (e.g. imidazolides or succinimides).

The reaction of an acid of formula II or a reactive functional derivative thereof with ethylenediamine according to variant a) of the above process can be carried out according to conventional methods. Thus, for example, a free acid of formula II can be reacted with ethylenediamine in the presence of a condensation agent in an inert solvent. If a carbodiimide such as dicyclohexylcarbodiimide is used as the condensation agent, then the reaction is conveniently carried out in an alkanecarboxylic acid ester such as ethyl acetate, an ether such as tetrahydrofuran or dioxane, a chlorinated hydrocarbon such as methylene chloride or chloroform, an aromatic hydrocarbon such as benzene, toluene or xylene, acetonitrile of dimethylformamide at a temperature between about −20° C. and room temperature, preferably at about 0° C. If phosphorus trichloride is used as the condensation agent, then the reaction is conveniently carried out in a solvent such as pyridine at a temperature between about 0° C. and the reflux temperature of the reaction mixture, preferably at about 90° C. In another embodiment of variant a), ethylenediamine is reacted with one of the aforementioned reactive functional derivatives of an acid of formula II. Thus, for example, a halide (e.g. the chloride) of an acid of formula II can be reacted at about 0° C. with ethylenediamine in the presence of a solvent such as diethyl ether.

The compounds of formula III in which $R^3$ is hydrogen and $R^4$ is a leaving group are, for example, N-(2-haloethyl)benzamides such as N-(2-chloroethyl)benzamide, N-(2-methylsulfonylethyl)benzamide or N-[2-(p-toluenesulfonyl)ethyl]benzamide and the like. The compounds of formula III in which $R^3$ and $R^4$ together are an additional bond are benzoylaziridines such as, for example, p-chlorobenzoylaziridine and the like.

In accordance with variant b) of the above process, a compound of formula III can be reacted with ammonia in a known manner at a temperature between about −40° C. and 50° C., if desired in the presence of a solvent such as dimethylformamide, dimethylacetamide, dimethyl sulfoxide and the like. The reaction is conveniently carried out in the presence of a solvent at about room temperature. When a benzoylaziridine of formula III is used, the reaction is preferably carried out in the presence of an inert solvent such as dimethylformamide, toluene or benzene.

The conversion of the group $R^5$ into the amino group in accordance with variant c) of the above process is likewise carried out in a known manner based on the nature of the group $R^5$. If $R^5$ is an amide group, then the conversion is conveniently carried out by acidic or basic hydrolysis. The acidic hydrolysis is advantageously carried out using a solution of a mineral acid such as hydrochloric acid, aqueous hydrogen bromide, sulfuric acid, phosphoric acid and the like in an inert solvent such as an alcohol (e.g. methanol or ethanol) or an ether (e.g. tetrahydrofuran or dioxane). The basic hydrolysis can be carried out using aqueous solutions of alkali metal hydroxides such as potassium hydroxide or sodium hydroxide. Inert organic solvents such as those mentioned above in connection with the acidic hydrolysis can be added as solubilizers. The acidic and basic hydroysis can be carried out in a temperature range of about room temperature to the reflux temperature of the mixture, with the boiling point of the mixture or a temperature slightly thereunder being preferred. If $R^5$ is the phthalimido group, then this can be converted in the amino group not only by acidic and basic hydrolysis, but also by aminolysis with an aqueous solution of a lower alkylamine such as methylamine or ethylamine. As the organic solvent there can be used a lower alkanol such as ethanol. This reaction is preferably carried out at room temperature. A third method for the conversion of the phthalimido group into the amino group comprises reacting compounds of formula IV in which $R^5$ is the phthalimido group with hydrazine in an inert solvent such as ethanol, a mixture of ethanol and chloroform, tetrahydrofuran or aqueous ethanol. The reaction temperature can be varied in a range of about room temperature to about 100° C., with the boiling point of the chosen solvent being preferred. The resulting product can be extracted with dilute mineral acids and can subsequently be obtained from the acidic solution by basification. The tert.-butoxycarbonylamino group is conveniently converted into the amino group using trifluoroacetic acid or formic acid in the presence or absence of an inert solvent at about room temperature, while the conversion of the trichloroethoxycarbonylamino group into the amino group is carried out using zinc or cadmium under acidic conditions. The acidic conditions are conveniently achieved by carrying out the reaction in acetic acid in the presence or absence of an additional inert solvent such as an alcohol (e.g. methanol). The benzyloxycarbonylamino group can be converted into the amino group in a known manner by acidic hydrolysis as described above or hydrogenolytically. The azido group can be reduced to the amino group according to known methods; for example, using elemental hydrogen in the presence of a catalyst such as palladium/carbon, Raney-nickel, platinum oxide and the like. A hexamethylenetetraammonium group can also be converted into the amino group by acidic hydrolysis according to known methods.

The compounds of formula II and their reactive functional derivatives used as starting materials in variant a) of the above process are known or can be prepared in analogy to the preparation of the known compounds.

The compounds of formula III used as starting materials in variant b) of the above process are likewise known or are analogues of known compounds and can be prepared in a known manner. Thus, for example, the compounds of formula III in which $R^3$ is hydrogen and $R^4$ is a leaving group can be prepared by reacting a compound of formula II or a reactive functional derivative thereof with ethanolamine under the reaction conditions described above in connection with variant a) and converting the resulting N-(2-hydroxyethyl)benzamide into the desired compound of formula III in a known manner; for example, by reaction with a halogenating agent such as phosphorus trichloride, phosphorus tribromide, phosphorus pentachloride, phosphorus oxychloride and the like, an arylsulfonyl halide such as tosyl chloride or an alkylsulfonyl halide such as mesyl chloride. A compound of formula III in which $R^3$ and $R^4$ together are an additional bond can be prepared, for example, by reacting a reactive functional derivative of a compound of formula II with ethyleneimine. The reaction can be carried out under the reaction conditions described above in connection with variant a).

The compounds of formula IV used as starting materials in variant c) of the above process are likewise known or are analogues of known compounds and can be prepared in a known manner. Thus, for example, a compound of formula II or a reactive functional derivative thereof can be reacted under the conditions described above in connection with variant a) with a compound of the general formula.

$$H_2N-CH_2-CH_2-R^5 \qquad V$$

wherein $R^5$ is as described above.

The compounds of formula V are known or can be prepared in analogy to the preparation of the known compounds.

In accordance with an alternative process, the compounds of formula IV in which $R^5$ is phthalimido, azido or hexamethyltetraammonium can be prepared by reacting a compound of formula III with potassium phthalimide, an alkali metal azide or hexamethylenetetramine. The reaction is carried out in a known manner under the reaction conditions described above in connection with variant b).

As mentioned above, the compounds of formula I and their pharmaceutically acceptable acid addition salts have monoamine oxidase (MAO) inhibiting activity. On the basis of this activity the compounds of formula I and their pharmaceutically acceptable acid addition salts can be used for the treatment of depressive states and Parkinsonism.

The MAO inhibiting activity of the compounds of formula I and their pharmaceutically acceptable addition salts can be determined using standard methods. Thus, the substances to be tested were administered orally to rats. Two hours thereafter the animals were killed and the MAO inhibiting activity was measured in homogenates of the brain and the liver according to the method described in Biochem. Pharmacol. 12 (1963) 1439-1441, but using phenethylamine ($2.10^{-5}$ mol. $1^{-1}$) in place of tyramine as the substrate. The thus-determined activity of representative compounds of formula I as well as their toxicity are evident from the following $ED_{50}$ values (μmol/kg, p.o. in rats) and $LD_{50}$ values (mg/kg, p.o. in mice), respectively:

| Compound | $ED_{50}$ | $LD_{50}$ |
|---|---|---|
| N-(2-Aminoethyl)-p-chlorobenzamide | 5.5 | 1000-2000 |
| N-(2-Aminoethyl)-p-fluorobenzamide | 4 | >5000 |
| N-(2-Aminoethyl)-p-bromobenzamide | 4 | 500-1000 |
| N-(2-Aminoethyl)-3,4-dichlorobenzamide | 10.3 | 1000-2000 |
| N-(2-Aminoethyl)-2,4-dichlorobenzamide | 1.5 | 625-1250 |
| N-(2-Aminoethyl)benzamide | 20 | >5000 |

The compounds of formula I and their pharmaceutically acceptable acid addition salts can be used as medicaments, for example in the form of pharmaceutical preparations. The pharmaceutical preparations can be administered orally (e.g. in the form of tablets, coated tablets, dragées, hard and soft gelatine capsules, solutions, emulsions or suspensions). The administration can, however also be carried out rectally (e.g. in the form of suppositories) or parenterally (e.g. in the form of injection solutions).

For the manufacture of tablets, coated tablets, dragées and hard gelatine capsules, the compounds of formula I and their pharmaceutically acceptable acid addition salts can be processed with pharmaceutically inert, inorganic or organic excipients. Examples of such excipients which can be used for tablets, dragées and hard gelatine capsules are lactose, maize starch or derivatives thereof, talc, stearic acid or its salts and the like.

Suitable excipients for soft gelatine capsules are, for example, vegetable oils, waxes, fats, semi-solid and liquid polyols and the like.

Suitable excipients for the manufacture of solutions and syrups are, for example, water, polyols, saccharose, invert sugar, glucose and the like.

Suitable excipients for injection solutions are, for example, water, alcohols, polyols, glycerine, vegetable oils and the like.

Suitable excipients for suppositories are, for example, natural or hardened oil, waxes, fats, semi-liquid or liquid polyols and the like.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain still other therapeutically valuable substances.

In accordance with the invention the compounds of formula I and their pharmaceutically acceptable acid addition salts can be used in the control or prevention of depressive states and Parkinsonism. The dosage can vary within wide limits and is, of course, fitted to the individual requirements in each particular case. In general, in the case of oral administration a daily dosage of about 10 to about 100 mg of a compound of formula I should be appropriate; although the upper limit given above can be exceeded should this be found to be indicated.

The following Examples illustrate the present invention, but are not intended to limit its extent. All temperatures are given in degrees Celsius.

EXAMPLE 1

18.5 g of ethyl 4-chlorobenzoate and 24 g of ethylenediamine are stirred at 130° for 17 hours. The mixture is cooled to room temperature, evaporated, and the residue is treated with 200 ml of ethyl acetate. The insoluble N,N'-ethylenebis(4-chlorobenzamide) (2.3 g), m.p. 266°-268°, is filtered off under suction, and the filtrate is washed three times with 50 ml of water each time and evaporated. The residue is treated with 100 ml of 1N hydrochloric acid, the insoluble N,N'-ethylenebis(4-chlorobenzamide) (1.0 g) is filtered off under suction, and the filtrate is evaporated to dryness. The residue is then evaporated twice with 100 ml of ethanol/benzene each time and recrystallized from ethanol/ether. There are obtained 13.7 g of N-(2-amino-ethyl)-4-chlorobenzamide hydrochloride, m.p. 216°-217°.

EXAMPLE 2

9.25 g of ethyl 4-chlorobenzoate and 16.0 g of N-(t-butoxycarbonyl)ethylenediamine are stirred at 130° for 15 hours. The mixture is cooled to room temperature, taken up in 100 ml of water and extracted three times with 50 ml of ethyl acetate each time. The ethyl acetate extract is washed twice with 50 ml of water each time, dried over sodium sulfate and evaporated to dryness. The crystalline residue is taken up in isopropyl ether and filtered off under suction. There are obtained 3.9 g of t-butyl [2-(4-chlorobenzamido)ethyl]carbamate, m.p. 141°-143°.

A solution of 2.8 g of t-butyl [2-(4-chlorobenzamido)ethyl]carbamate in 50 ml of formic acid is left to stand at room temperature for 1.5 hours. The mixture is then concentrated to dryness, and the residue is dissolved in 50 ml of hydrochloric acid(1:1; volume/volume). The solution is concentrated, the residue is evaporated twice with ethanol/benzene and then recrystallized from ethanol. There are obtained 2.1 g of N-(2-aminoethyl)-4-chlorobenzamide hydrochloride which is identical with the product obtained in Example 1.

EXAMPLE 3

23 ml (0.17 mol) of triethylamine are added dropwise at 0° to a suspension of 23.5 g (0.15 mol) of 4-chlorobenzoic acid and 15 ml (0.16 mol) of ethyl chloroformate in 200 ml of chloroform. After completion of the addition (0.5 hour), the solution obtained is added dropwise at 0° to a solution of 50 ml (0.75 mol) of ethylenediamine in 100 ml of chloroform. After completion of the reaction, 115 ml of concentrated hydrochloric acid are added dropwise at 0°. The acidic mixture is filtered and the neutral constituents remaining are removed by extraction with chloroform. The aqueous phase is then made alkaline with sodium hydroxide solution and extracted several times with chloroform. The chloroform extracts are dried and concentrated. The residue is converted into the hydrochloride which is recrystallized from ethanol/ether. There are obtained 15.1 g of N-(2-aminoethyl)-4-chlorobenzamide hydrochloride, m.p. 212°-214°. The free base melts at 43°-45°.

EXAMPLE 4

19.1 g (0.1 mol) of 2,4-dichlorobenzoic acid are suspended in 200 ml of methylene chloride and brought into solution by adding 15.3 ml (0.11 mol) of triethylamine. 10 ml (0.1 mol) of ethyl chloroformate are then added dropwise at 0°. After completion of the addition (0.5 hour), the mixture is poured on to ice/water. The methylene chloride phase is separated, dried over magnesium sulfate and concentrated to about 30 ml. This solution is added dropwise at 0° to a solution of 20 ml (0.3 mol) of ethylenediamine in 100 ml of tetrahydrofuran. After completion of the addition (0.5 hour), the mixture is filtered, the filtrate is acidified with dilute hydrochloric acid the neutral constituents are removed by extraction with ethyl acetate. The aqueous phase is made alkaline with sodium hydroxide solution and extracted several times with chloroform. After drying and concentrating the chloroform phases, the residue is converted into the hydrochloride. After recrystallization from ethanol/ether, there are obtained 7.1 g of N-(2-aminoethyl)-2,4-dichlorobenzamide hydrochloride, m.p. 179°-182°.

EXAMPLE 5

22.1 ml (0.16 mol) of triethylamine are added dropwise at 10° to a suspension of 23.5 g (0.15 mol) of 2-chlorobenzoic acid in 200 ml of chloroform. 14.8 ml (0.155 mol) of ethyl chloroformate are then added dropwise at the same temperature. After completion of the addition (1 hour), the mixture is poured on to ice/water. The chloroform phase is separated, dried over magnesium sulfate and gently concentrated to about 60 ml. The thus-obtained solution is added dropwise at 10° to a solution of 40.1 ml (0.6 mol) of ethylenediamine in 400 ml of chloroform. After completion of the addition, the difficulty soluble neutral constituents are filtered off, the filtrate is concentrated and excess ethylenediamine is removed in a high vacuum. The residue obtained (31.5 g) is converted into the hydrochloride which is purified by recrystallization from ethanol/ether. There are obtained 19.2 g of N-(2-aminoethyl)-2-chlorobenzamide hydrochloride (see Example 6 of German Offenlegungsschrift 2.362.568), m.p. 155°-158°. An analytically pure sample melts at 159°-161°.

In an analogous manner, from 23.5 g (0.15 mol) of 3-chlorobenzoic acid there were obtained 13.5 g of N-(2-aminoethyl)-3-chlorobenzamide hydrochloride (see Example 7 of German Offenlegungsschrift 2.616.486), m.p. 201°–203°. The free base melts at 69°–71° (from ethyl acetate/n-hexane).

EXAMPLE 6

24.4 g (0.02 mol) of benzoic acid are reacted with triethylamine and ethyl chloroformate in a manner analogous to that described in Example 5 and added dropwise at 10° to a solution of 53.5 ml (0.8 mol) of ethylenediamine in 750 ml of chloroform. After removing the difficulty soluble neutral constituents by filtration, the chloroform solution is concentrated and excess ethylenediamine is removed in a high vacuum. The oily residue (36.3 g) is taken up in 200 ml of 2N sodium hydroxide solution, saturated with solid sodium chloride and extracted several times with ethyl acetate. The ethyl acetate extracts are dried over magnesium sulfate and concentrated. The product is converted into the hydrochloride which is purified by recrystallization from ethanol, there being obtained 5.2 g of N-(2- aminoethyl)benzamide hydrochloride [J. Amer. Chem. Soc. 61, 822 (1939)], m.p. 163°–165°.

EXAMPLE 7

To a suspension of 6.4 g (0.04 mol) of 4-methoxybenzoic acid in 60 ml of chloroform are added dropwise at 10°, 5.5 ml (0.04 mol) of triethylamine and then 3.8 ml (0.04 mol) of ethyl chloroformate. The solution obtained is then added dropwise at 5° to a solution of 10.7 ml (0.16 mol) of ethylenediamine in 100 ml of chloroform. After stirring at room temperature for 2 hours, the mixture is filtered. The filtrate is concentrated under reduced pressure and then excess ethylenediamine is removed in a high vacuum. The residue is acidified with dilute hydrochloric acid and extracted several times with ethyl acetate. The aqueous phase is made alkaline with 28% sodium hydroxide solution and extracted three times with chloroform. After drying and concentrating the chloroform extracts, the residue is converted into the hydrochloride. By recrystallization from ethanol/ether there are obtained 3.4 g of N-(2-aminoethyl)-4-anisamide hydrochloride (see Example 7 of German Offenlegungsschrift 2.616.486), m.p. 186°–189°. The free base melts at 37°–38°.

In a manner analogous to that described above,
from 20.4 g (0.15 mol) of 4-methylbenzoic acid there were obtained 8.7 g of N-(2-aminoethyl)-4-toluamide hydrochloride (see Example 6 of German Offenlegungschrift 2.616.486), m.p. 164°–166°;
from 17.2 g (0.09 mol) of 3,4-dichlorobenzoic acid there were obtained 9.1 g of N-(2-aminoethyl)-3,4-dichlorobenzamide hydrochloride, m.p. 183°–185°; the free base melts as 98°–100°;
from 12.2 g (0.08 mol) 2-methoxybenzoic acid there were obtained 9.3 g of N-(2-aminoethyl)-2-anisamide hydrochloride (see Example 6 of German Offenlegungsschrift 2.362.568), m.p. 109°–111°;
from 12.2 g (0.08 mol) of 3-methoxybenzoic acid there were obtained 6.2 g of N-(2-aminoethyl)-3-anisamide hydrochloride, m.p. 96°–98°;
from 3.9 g (0.015 mol) of 5-dimethylsulfamoyl-2-methoxybenzoic acid there were obtained 1.4 g of N-(2-aminoethyl)-5-(dimethylsulfamoyl)-2-anisamide hydrochloride, m.p. 193°–195° (decomposition). The free base melts at 118°–123°.

EXAMPLE 8

In a manner analogous to that described in Example 7, 11.8 g (0.08 mol) of 4-cyanobenzoic acid are reacted with triethylamine and ethyl chloroformate and worked-up and then added dropwise to a solution of 21.4 ml of ethylenediamine in 350 ml of chloroform. After adding 45 ml of dimethylformamide, the mixture is heated to 60° for a further 1 hour. After filtration, the filtrate is concentrated, and the residue is treated in the same manner as described in Example 7. There are obtained 3.5 g of N-(2-aminoethyl)-4-cyanobenzamide hydrochloride, m.p. 212°–215° (decomposition). The free base melts at 124°–126°.

In an analogous manner, from 4.5 g (0.023 mol) of 4-trifluoromethylbenzoic acid there were obtained 3.1 g of N-(2-aminoethyl)-α,α,α-trifluoro-4-toluamide hydrochloride, m.p. 196°–199°; the free base melts at 66°–68°.

EXAMPLE 9

A solution of 6.2 ml (0.05 mol) of 4-chlorobenzoyl chloride in 150 ml of ether is added dropwise at −10° over a period of 0.5 hour to a solution of 10 ml (0.15 mol) of ethylenediamine in 150 ml of ether. The mixture is left to warm to room temperature, filtered and the white residue is rinsed twice with ether. After concentrating the ether solution, the residue is acidified with dilute hydrochloric acid and extracted several times with ethyl acetate in order to remove the neutral constituents. The aqueous phase is made alkaline with sodium hydroxide solution and extracted several times with chloroform. After evaporating the chloroform, converting the residue into the hydrochloride and recrystallization from ethanol/ether, there are obtained 1.8 g of N-(2-aminoethyl)-4-chlorobenzamide hydrochloride which is identical with the product obtained in Example 1.

In an analogous manner, from 7 ml (0.05 mol) of 2,4-dichlorobenzoyl chloride there were obtained 1.7 g of N-(2-aminoethyl)-2,4-dichlorobenzamide hydrochloride of melting point 178°–179° which is identical with the product obtained in Example 4.

EXAMPLE 10

7 g (0.039 mol) of methyl 3,4-methylenedioxybenzoate and 8.5 ml (0.126 mol) of ethylenediamine are heated to 100° (bath temperature) for 2.5 hours. After cooling, the excess ethylenediamine is removed in a high vacuum. The residue is acidified with dilute hydrochloric acid and extracted with chloroform. The aqueous phase is made alkaline with sodium hydroxide solution and then extracted several times with chloroform. After evaporating the solvent and recrystallizing the residue from chloroform/hexane, there are obtained 3.4 g of N-(2-aminoethyl)-1,3-benzdioxol-5-carboxamide, m.p. 120°–123°. The hydrochloride melts at 210°–213°.

EXAMPLE 11

10.7 g (0.05 mol) of methyl 4-bromobenzoate and 10.4 ml (0.15 mol) of ethylenediamine are heated to 130° (bath temperature) for 30 minutes. After working-up in a manner analogous to that described in Example 10 and recrystallization from methanol/ether, there are obtained 6.5 g of N-(2-aminoethyl)-4-bromobenzamide hydrochloride, m.p. 229°–232°.

EXAMPLE 12

10.7 ml (0.16 mol) of ethylenediamine are added to 6.65 g (0.04 mol) of methyl 4-methoxybenzoate. The solution is heated to 130° (bath temperature) for 2 hours and, after cooling, excess ethylenediamine is removed in a high vacuum. The residue is acidified with dilute hydrochloric acid. The difficulty soluble neutral constituents are removed by filtration and subsequent extraction with ethyl acetate. The aqueous phase is made alkaline with 28% sodium hydroxide solution, saturated with sodium chloride and extracted three times with chloroform. The chloroform extracts are dried over magnesium sulfate and concentrated. The reside is converted into the hydrochloride which is recrystallized from ethanol/ether. There are obtained 3.8 g of N-(2-aminoethyl)-4-anisamide hydrochloride (see Example 7 of German Offenlegungsschrift 2.616.486), m.p. 201°-204°.

In an analogous manner, from 20 g (0.1 mol) of methyl 4-chloro-2 -methoxybenzoate and 20.1 ml (0.3 mol) of ethylenediamine there were obtained 8.9 g of N-(2-aminoethyl) -4-chloro-2-anisamide hydrochloride, m.p. 132°-135°. (decomposition).

EXAMPLE 13

7.7 g (0.05 mol) of methyl 4-fluorobenzoate and 10 ml (0.15 mol) of ethylene diamine are heated to 130° (bath temperature) for 2 hours. The mixture is poured on to ice/hydrochloric acid and extracted with ethyl acetate in order to remove the neutral constituents. The aqueous phase is made alkaline with sodium hydroxide solution and extracted several times with chloroform. After drying and concentrating the chloroform extracts, the residue (7.6 g) is recrystallized from ethyl acetate/hexane, the being obtained N-(2-aminoethyl)-4-fluorobenzamide, m.p. 57°-60°. The hydrochloride melts at 214°-216°.

EXAMPLE 14

A solution of 1.3 ml (0.01 mol) of 4-chlorobenzoyl chloride in 15 ml of chloroform is added dropwise at 0° to a solution of 1.02 g (0.01 mol) of acetylethylenediamine [J. Amer. Chem. Soc. 61, 822 (1939)] and 1.4 ml (0.01 mol) of triethylamine in 25 ml of chloroform. After 15 minutes, the resulting crystals are filtered off, washed with chloroform and dried. There are obtained 1.9 g of N-(2-acetylaminoethyl)-4-chlorobenzamide, m.p. 222°-224°.

In order to cleave the protecting group, the N-(2-acetylaminoethyl)-4-chlorobenzamide obtained is heated to reflux for 22 hours in a mixture of 24 ml of 2N hydrochloric acid and 15 ml of ethanol. After concentrating the solution, the product is recrystallized from ethanol/ether. There are obtained 1.2 g of N-(2-aminoethyl-4-chlorobenzamide hydrochloride, m.p. 211°-213°, which is identical with the product obtained in Example 1.

EXAMPLE 15

2.6 ml (0.02 mol) of 4-chlorobenzoyl chloride are added dropwise at 0° to a solution of 1.2 ml (0.02 mol) of ethanolamine and 3 ml (about 0.02 mol) of triethylamine in 30 ml of methylene chloride. The mixture is then poured into dilute hydrochloric acid and extracted twice with methylene chloride. The methylene chloride extracts are dried over magnesium sulfate and concentrated. After purification on silica gel using chloroform and chloroform/methanol 9:1) as the eluting agent, there are obtained 3.1 g of N-(2-hydroxyethyl)-4-chlorobenzamide.

A solution of 0.6 ml of methanesulfonyl chloride in 3 ml of methylene chloride is added dropwise at 0° to a solution of 1.5 g (0.0075 mol) of N-(2-hydroxyethyl)-4-chlorobenzamide and 1 ml of triethylamine in 15 ml of methylene chloride. After 15 minutes, the mixture is poured on to ice/water and extracted. There are obtained 2.1 g of N-(2-methylsulfonyloxyethyl)-4-chlorobenzamide in crystalline form which is used in the next step without further purification.

The N-(2-methylsulfonyloxyethyl)-4-chlorobenzamide obtained is dissolved in 5 ml of dimethylformamide and added dropwise at room temperature to a solution of ammonia in dimethylformamide. After stirring for 2 hours, the mixture is worked-up and there is obtained N-(2-aminoethyl)-4-chlorobenzamide which is identical with the product obtained in Example 1.

EXAMPLE A

| Interlocking gelatine capsules (5 mg) | |
|---|---|
| Ingredients: | |
| 1. N-(2-Aminoethyl)-2,4-dichlorobenzoamide hydrochloride | 5.78 mg*) |
| 2. Lactose (powdered) | 80.22 mg |
| 3. Maize starch | 40.00 mg |
| 4. Talc | 3.60 mg |
| 5. Magnesium stearate | 0.40 mg |
| 6. Lactose (crystalline) | 110.00 mg |
| Capsule fill weight | 240.00 mg |

*)corresponding to 5 mg of base.

Procedure 1-5 are mixed and the mixture is sieved through a sieve having a mesh size of 0.5 mm. 6 is then added and the resulting mixture is mixed. This finished mixture is filled into interlocking gelatine capsules of suitable size (e.g. No. 2) having an individual fill weight of 240 mg.

EXAMPLE B

| Tablets (5 mg) | |
|---|---|
| Ingredients: | |
| 1. N-(2-Aminoethyl)-2,4-dichlorobenzamide hydrochloride | 5.78 mg*) |
| 2. Lactose (powdered) | 104.22 mg |
| 3. Maize starch | 45.00 mg |
| 4. Polyvinylpyrrolidone K 30 | 15.00 mg |
| 5. Maize starch | 25.00 mg |
| 6. Talc | 4.50 mg |
| 7. Magnesium stearate | 0.50 mg |
| Tablet weight | 200.00 mg |

*)corresponding to 5 mg of base.

Procedure 1-3 are mixed and the mixture is sieved through a sieve having a mesh size of 0.5 mm. This powder mixture is moistened with an alcoholic solution of 4 and kneaded. The moist mass is granulated, dried and converted into a suitable particle size. 5, 6 and 7 are added in succession to the dried granulate and the resulting mixture is mixed. The finished mixture is pressed to tablets of suitable size having an individual weight of 200 mg.

EXAMPLE C

| Interlocking gelatine capsules (10 mg) | | |
|---|---|---|
| Ingredients: | | |
| 1. | N-(2-Aminoethyl)-p-chlorobenzamide hydrochloride | 11.84 mg*) |
| 2. | Lactose (powdered) | 74.16 mg |
| 3. | Maize starch | 40.00 mg |
| 4. | Talc | 3.60 mg |
| 5. | Magnesium stearate | 0.40 mg |
| 6. | Lactose (crystalline) | 110.00 mg |
| | Capsule fill weight | 240.00 mg |

*)corresponding to 10 mg of base.

Procedure 1-5 are mixed and the mixture is sieved through a sieve having a mesh size of 0.5 mm. 6 is then added and the resulting mixture is mixed. This finished mixture is filled into interlocking gelatine capsules of suitable size (e.g. No. 2) having an individual fill weight of 240 mg.

EXAMPLE D

| Tablets (10 mg) | | |
|---|---|---|
| Ingredients: | | |
| 1. | N-(2-Aminoethyl)-p-chlorobenzamide hydrochloride | 11.84 mg*) |
| 2. | Lactose (powdered) | 103.16 mg |
| 3. | Maize starch | 40.00 mg |
| 4. | Polyvinylpyrrolidone K 30 | 15.00 mg |
| 5. | Maize starch | 25.00 mg |
| 6. | Talc | 4.50 mg |
| 7. | Magnesium stearate | 0.50 mg |
| | Tablet weight | 200.00 mg |

*)corresponding to 10 mg of base.

Procedure 1-3 are mixed and the mixture is sieved through a sieve having a mesh size of 0.5 mm. This powder mixture is moistened with an alcoholic solution of 4 and kneaded. The moist mass is granulated, dried and converted into a suitable particle size. 5, 6 and 7 are added in succession to the dried granulate and the resulting mixture is mixed. The finished mixture is pressed to tablets of suitable size having an individual weight of 200 mg.

We claim:

1. A method for controlling or preventing depressive states which comprises administering to a host in need of such treatment an effective amount of a compound of the formula

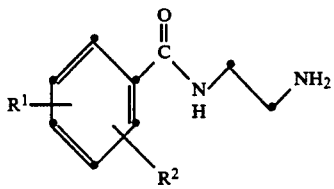

wherein $R^1$ is halogen and $R^2$ is hydrogen or halogen, or a pharmaceutically acceptable acid addition salt thereof.

2. The method according to claim 1 wherein the compound being administered is N-(2-aminoethyl)-p-chlorobenzamide or a pharmaceutically acceptable acid addition salt thereof.

3. The method according to claim 1 wherein the compound being administered is N-(2-aminoethyl)-p-fluorobenzamide or a pharmaceutically acceptable acid addition salt thereof.

4. The method according to claim 1 wherein the compound being administered is N-(2-aminoethyl)-p-bromobenzamide or a pharmaceutically acceptable acid addition salt thereof.

5. The method according to claim 1 wherein the compound being administered is N-(2-aminoethyl)-3,4-dichlorobenzamide or a pharmaceutically acceptable acid addition salt thereof.

6. The method according to claim 1 wherein the compound being administered in N-(2-aminoethyl)-2,4-dichlorobenzamide or a pharmaceutically acceptable acid addition salt thereof.

* * * * *